(12) United States Patent
Pan et al.

(10) Patent No.: US 10,529,132 B2
(45) Date of Patent: Jan. 7, 2020

(54) METHOD FOR REAL-TIME CUTTING OF DIGITAL ORGAN BASED ON METABALL MODEL AND HYBRID DRIVING METHOD

(71) Applicant: BEIHANG UNIVERSITY, Beijing (CN)

(72) Inventors: JunJun Pan, Beijing (CN); Shizeng Yan, Beijing (CN); Qinping Zhao, Beijing (CN)

(73) Assignee: BEIHANG UNIVERSITY, Beijing (CN)

( * ) Notice: Subject to any disclaimer, the term of this patent is extended or adjusted under 35 U.S.C. 154(b) by 0 days.

(21) Appl. No.: 15/835,408

(22) Filed: Dec. 7, 2017

(65) Prior Publication Data
US 2018/0204378 A1    Jul. 19, 2018

(30) Foreign Application Priority Data

Jan. 13, 2017    (CN) .......................... 2017 1 0023932

(51) Int. Cl.
*G06T 17/20*    (2006.01)
*G06T 17/30*    (2006.01)
(Continued)

(52) U.S. Cl.
CPC ............ *G06T 17/205* (2013.01); *A61B 34/10* (2016.02); *G06T 17/30* (2013.01); *G06T 19/20* (2013.01);
(Continued)

(58) Field of Classification Search
CPC .............. A61B 34/10; A61B 2034/105; A61B 2034/104; G06T 19/20; G06T 17/30; G06T 17/205; G06T 2210/21; G06T 2210/41
See application file for complete search history.

(56) References Cited

U.S. PATENT DOCUMENTS

2013/0172904 A1*    7/2013    Ikits .................... G06T 17/10
                                                          606/130

FOREIGN PATENT DOCUMENTS

CN    103699714 A         4/2014
CN    104318056 A    *    1/2015
(Continued)

OTHER PUBLICATIONS

J. Pan etal., Metaballs-based physical modeling and deformation of organs for virtual surgery; The Visual Computer, Jun. 2015, vol. 31, Issue 6-8, pp. 947-957 (Year: 2015).*

(Continued)

*Primary Examiner* — Michael Le
(74) *Attorney, Agent, or Firm* — J.C. Patents (57) ABSTRACT

Disclosed is a method for real-time cutting of digital organ based on a metaball model and a hybrid driving method, including a cutting procedure for driving a model using a position-based dynamics and a meshless method, a cutting mode which begins from a metaball driven by the position-based dynamics, proceeds to a point set driven by the meshless method and then create a new metaball. The method includes: a preprocessing procedure which performs an initialization operation while reading a model file; a deforming procedure which drives a model using a method based on the position-based dynamics; a cutting procedure which drives the model using the hybrid driving method and performs cutting using said cutting mode; and a rendering procedure which renders the model during the second and third procedures.

3 Claims, 6 Drawing Sheets

Cutting of a cholecyst (51) Int. Cl.
  *G06T 19/20* (2011.01)
  *A61B 34/10* (2016.01)
(52) U.S. Cl.
  CPC ... *A61B 2034/104* (2016.02); *A61B 2034/105* (2016.02); *G06T 2210/21* (2013.01); *G06T 2210/41* (2013.01); *G06T 2219/008* (2013.01); *G06T 2219/2021* (2013.01)

(56) References Cited

FOREIGN PATENT DOCUMENTS

| CN | 104318056 A | 1/2015 |
| CN | 105302972 A | 2/2016 |
| CN | 105559887 A | 5/2016 |
| CN | 106156537 A | 11/2016 |
| JP | 2015-127965 A | 7/2015 |

OTHER PUBLICATIONS

CN104318056A (Machine Translation on Mar. 18, 2019) (Year: 2015).*
Xiaohu Guo, Meshless Thin-shell Simulation Based on Global Conformal Parameterization; IEEE Transactions on Visualization and Computer Graphics, vol. XX, No. Y, Month 2006 (Year: 2006).*
Guo, Xiaohu et al., "Meshless Thin-Shell Simulation Based on Global Conformal Parameterization" IEEE Transactions on Visualization and Computer Graphics, vol. 12, No. 3, (May/Jun. 2006), pp. 375-385.
Pan, Junjun et al., "Metaball-based physical modeling and deformation of organs for virtual surgery" The Visual Computer: International Journal of Computer Graphics archive, vol. 31, (Jun. 2015), pp. 947-957.
The Chinese First Examination Report of corresponding Chinese application No. 201710023932.1, dated Jun. 5, 2019.

\* cited by examiner

Cutting of a liver

FIG. 7

Cutting of a spleen

METHOD FOR REAL-TIME CUTTING OF DIGITAL ORGAN BASED ON METABALL MODEL AND HYBRID DRIVING METHOD

CROSS-REFERENCE TO RELATED APPLICATION

This application claims priority to Chinese Patent Application No. 201710023932.1, filed on Jan. 13, 2017, which is hereby incorporated by reference in its entirety.

TECHNICAL FIELD

The present disclosure relates to a method for real-time cutting of digital organ based on a metaball model and a hybrid driving method, and belongs to the technical field of virtual surgery, and may also be applied in related fields, including animation and gaming.

BACKGROUND

A laparoscopic surgery is one of the procedures commonly used in modern healthcare, which is significant for treating patients. However, a great number of novice physicians need extensive training in order to be skilled in performing the procedure. At present, most surgical trainings in domestic hospitals are carried out using a substitution, the use of which has shortcomings such as inaccuracy and limited supplies. With continuous development of computer technologies, the virtual reality technology is gradually coming out, but also presents a new approach for surgery trainings, e.g. the virtual laparoscopic surgery.

In practice, the surgery involves various operations, such as touching, cutting, hemostasis, suture and the like. During the virtual surgery, it is desirable to replicate as many of these interactions as possible. Generally, establishment of a virtual surgery includes modeling, deformation driving, cutting, suture and the like. For organs at different locations, additional realistic features may be included according to their characteristics, such as blood, vascular vessels and the like. A volume model will be modeled for an organ subsequent to acquisition of its skin model by scanning. Common volume models include tetrahedral model, hexahedral model, metaball model and particle model. The driving involves addition of a physical or geometric driving method to the model, and commonly-used methods include mass spring method, finite element method and meshless method. The cutting and suture relate to handling changes in topology.

In the existing cutting method, most of the models used are the tetrahedral model or the hexahedral model. The tetrahedral model will produce more accurate splitting edges during cutting, but has a huge calculation, likely leading to an abnormal tetrahedron and more trouble for subsequent works. The hexahedral model determines the cutting edges through constant subdivisions, which require more smoothing operations. The conventional cutting methods based on the metaball model generally perform subdivision of metaballs by way of the octree, which tends to produce excessive small metaballs after the subdivision, and significantly increases boundary conditions while reducing the iterative speed, leading to difficulties for processing.

SUMMARY

The present disclosure solves a technical problem associated with conventional model, which are insufficient convergence speed and a tendency to generate excessive fragment models when being sub-divided. The metaball model selected and used in the present disclosure is essentially similar to the hexahedral model, except for providing a smoother model, with a connection topology being indirectly constructed based on a capacity to allow overlapping. Another advantage for using the metaball model lies in less filling amount and higher rate of convergence. Accordingly, a method for real-time cutting of a digital organ based on a metaball model and a hybrid driving method is provided. In this method, the metaball model is used to perform deforming and cutting, providing a deforming solution with realistically rapid convergence speed. For the cutting, an accurate and rapid splitting and merging method may be provided to meet real-time and authenticity demanded in a virtual surgery system.

The technical solution used in the present disclosure is a method for real-time cutting of digital organ based on a metaball model and a hybrid driving method. Starting from the basis of a metaball model, a position-based dynamics and a meshless method are used during a cutting procedure to drive a model. In order to solve problems such as frequent splitting and merging of metaballs during the cutting procedure, a cutting mode which begins from metaball, proceeds to point set and then back to metaball is used. In this mode, the position-based dynamics method is used to drive the metaball, and the meshless method is used to drive the point set generated from the metaball. The method includes four steps: firstly, a preprocessing procedure which performs some initialization operations while reading a model file; secondly, a deforming procedure which drives a model using a method based on the position-based dynamics; thirdly, a cutting procedure which drives the model to deform using a combination of metaball and point set and performs cutting using a method that starts from metaball, proceeds to point set and then back to metaball; and fourthly, a rendering procedure which performs rendering for the model during the second and third procedures. The present disclosure is capable of realistically simulating a procedure of cutting soft tissues during a virtual surgery and has high controllability and real-time responsiveness.

The present disclosure specifically includes four steps as follows.

Step 1: a preprocessing procedure, including: reading a model to be processed, where the model includes a metaball model and a surface model, the metaball model being a physical model configured for driving, and the surface model being a geometrical model configured for rendering; the preprocessing procedure further includes initializing a rendering environment and a deforming method;

Step 2: a deforming procedure, including: performing a position-based dynamics method driving according to data obtained by reading the model as in the Step 1, where the deforming procedure is a loop procedure in that the deforming procedure repeats at the end of the processing unless a cutting procedure in Step 3 is performed or a scalpel is disengaged from the surface of the model;

Step 3: a cutting procedure, contingent upon a cutting event which occurs at the end of Step 2 when a scalpel collides with the metaball model, including: going to the deforming procedure of Step 2 if termination does not occur at the end of the cutting procedure; involving a hybrid deforming and driving processing procedure during the cutting procedure, where the hybrid driving processing procedure uses a cutting mode that begins from a metaball, proceeds to a point set, and then back to a metaball, where a metaball cutting includes four parts, which are, firstly, converting collided metaball into a point set; then constructing a meshless system using the point set while coupling the remains of the metaball system and the meshless system; and finally, converting the point set into a metaball; and a surface cutting, which occurs together with the metaball cutting, includes splitting a surface, generating a fissure and re-binding; and Step 4: a rendering procedure, which has been ready starting from the Step 1, requires data input from the deforming procedure or the cutting procedure as the Step 2 and the Step 3 proceed, performs rendering constantly, and finally outputs a display image corresponding to the model.

The preprocessing procedure in Step 1 is implemented by:

(1) reading three types of pre-established files, where the three types of files are a standard triangular patch OBJ file, a standard texture image TGA file and a custom metaball SPH file, where the SPH file is generated via the OBJ file, the SPH file provides metaball information which includes metaball centroid position and radius information; the OBJ file stores vertex information and patch information of a triangular patch in a generic form; the TGA file stores texture information; and data read from the three types of files are stored using a corresponding data structure, respectively;

(2) initializing the rendering environment, including constructing an OpenGL rendering environment and initializing a rendering environment for a 3D tactile device Phantom Device, which may include, for example, configuring an illuminating parameter and a physical parameter, such as friction factor, elasticity modulus, etc.; and (3) initializing a physical driving method, including initializing a parameter and a dependent variable for the position-based dynamics method and a meshless method.

The deforming procedure in Step 2 is implemented by:

(1) driving the metaball using the position-based dynamics (PBD) method according to the data obtained by reading the model as in the Step 1; adding a stretch restraint, a unit restraint and an energy restraint into the position-based dynamics method; and arranging fixed metaball in order to achieve convergence; and (2) establishing Gaussian binding between a vertex of a surface triangular patch and a metaball, so that the movement of the vertex is determined by the movement of at most 3 metaballs surrounding the vertex, where the determination is such that a Gaussian value for a ratio of a distance between a metaball centroid and the vertexes to the radius is applied with a weight upon the vertex.

The cutting procedure in Step 3 is implemented by:

(1) converting the metaball into the point set when a scalpel collides with the metaball, where denser sampling leads to more precise outcome, while removing any collided metaball to generate a residual metaball system;

(2) constructing the meshless system using the point set generated in Step (1); performing the driving using a meshless method which is a simplified meshless method with faster calculation speed;

(3) performing the hybrid driving using the residual metaball system generated in Step (1) and the meshless system generated in Step (2), where the two systems are coupled in that movement in one system causes movement information being fed back to the other system;

(4) restoring the point set back to a metaball when the scalpel disengages from the metaball model, where the restoring is realized by collecting a meshless point on a cut surface, analyzing the vertex using a Voronoi diagram method to obtain a central skeleton, and filling the skeleton with a metaball;

(5) splitting a surface triangle into a more appropriate triangle based on various conditions in which a scalpel cutting line intersects with the triangle, where the splitting follows a basic principle, that is, a split surface remains being filled with a triangle, polygons on different sides of the cutting line are separately split into more desirable triangles; collecting a meshless point at a fissure; triangulating the meshless point to generate a fissured mesh; and updating binding condition for all triangles. The triangles that need to be updated include newly generated triangles and triangles near the fissure; and (6) the time logic for the disclosed Step 3 includes: executing the above steps according to the following time logic: performing Step (1) when the scalpel collides with the metaball, and potentially repeating the step for several times; proceeding to Step (2) and Step (3) immediately after each time Step (1) is performed, where the cutting is completed when no more collision occurs between the scalpel and the metaball; proceeding to Step (4); performing the Step (5) in parallel with other steps because the splitting is required whenever the scalpel collides with the surface; generating the fissure while restoring the metaball in Step (4); and performing re-binding after both Step (4) and the fissure generation are completed.

The rendering procedure in Step 4 is implemented by:

(1) drawing surface information for the model, where the surface information includes three parts: texture information, vertex information and patch information, initial information of the surface has been given when the mode is read, the texture information remains unchanged, the vertex information is changed continuously during the deforming procedure and the cutting procedure, the patch information is also changed during the steps of the cutting procedure, the rendering procedure accompanies both the deforming procedure and the cutting procedure, the surface information needs to be drawn twice, one on a screen using OpenGL, another drawn into a force feedback device using a Phantom library;

(2) selectively drawing volume information; providing a volume drawing switch; opening the volume information for drawing when viewing a cutting effect, where the volume information includes the metaball information and metaball topology information, the metaball information being given during the preprocessing procedure when the model is read, and later being continuously changed during the steps of the deforming procedure and the cutting procedure, the metaball topology information indicating the intersection between the metaball in that a line segment connects the centroids of intersecting metaballs to indicate the existence of topology information therebetween.

Compared with the prior art, the present disclosure is advantageous in that:

In terms of the model: a conventional cutting method typically fills the interior of an organ with tetrahedrons or hexahedrons having edges and corners. Due to the complexity of the organ and uniformity of a constructed model, a large number of identical models with similar volumes are often seen in the filling, which leaves the convergence to fall behind the deforming procedure, harming the authenticity. Instead, by using metaballs for the filling, advantage may be achieved in terms of less filling and faster convergence. Moreover, the metaball is particularly suitable for collision detection, which greatly reduces calculation time and improves frame rates, streamlining the cutting procedure.

In terms of the driving method: the position-based dynamics model is, although not physically precise, a very good approximation to a physical deforming method. This method has the advantages of less calculation workload and fast deforming speed. However, the meshless model is a physically precise model, which performs well in maintaining details. Using the meshless method to conduct fine scale deformation can, with stability, better preserve details in the model. The present disclosure chooses the position-based dynamics method to drive the metaball, and uses the meshless method to drive an intermediate model generated from the metaball, thereby striking a balance between accuracy and calculation workload, with an accurate and precise cutting.

In addition, the present disclosure also incorporates a 3D tactile device which, when bound to surgical instruments, such as surgical clamp and a scalpel, used in a practical surgery, is capable of realistically re-producing surgical environment.

DESCRIPTION OF EMBODIMENTS

Figure 1:
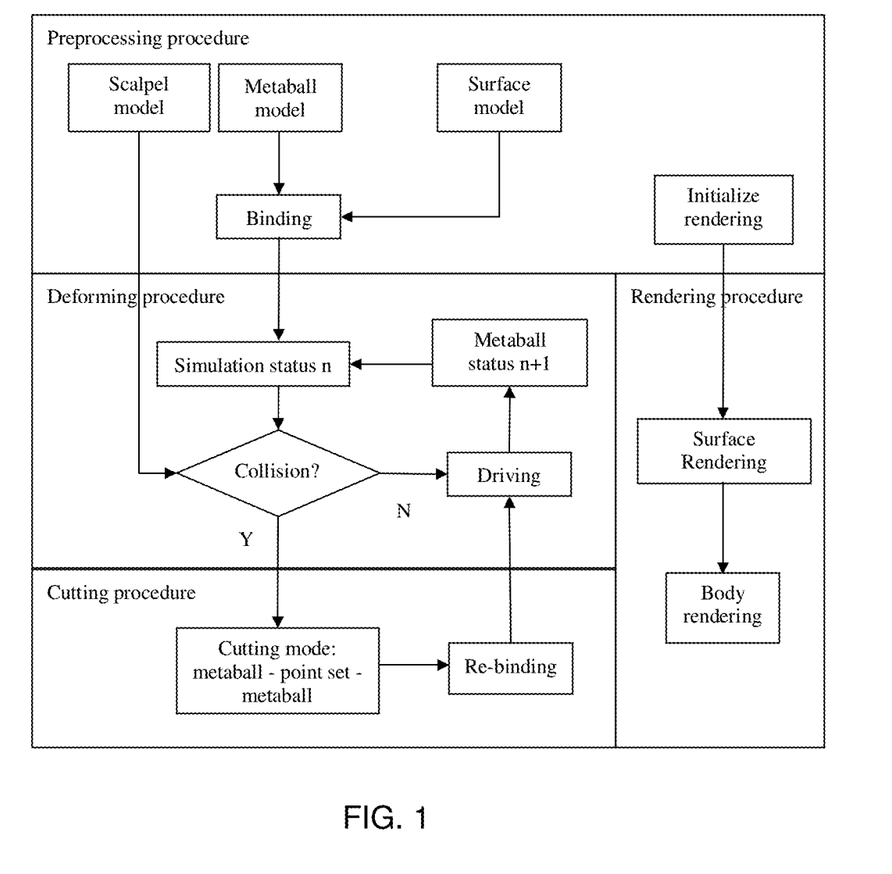
FIG. 1 is a flowchart illustrating a procedure of method for real-time cutting of a digital organ based on a metaball model and a hybrid driving method according to the present disclosure.

As shown in FIG. 1, a flowchart illustrating a procedure of method for real-time cutting of a digital organ based on a metaball model and a hybrid driving method according to the present disclosure, the method may be divided into four steps: a preprocessing procedure, a deforming procedure, a cutting procedure and a rendering procedure. The four steps are not performed sequentially. Rather, the method begins from the preprocessing procedure, then proceeds to the deforming procedure, then the cutting procedure when a cutting event occurs, and returns to the deforming procedure after the cutting procedure is completed. The rendering procedure accompanies the deforming procedure and the cutting procedure, i.e. rendering is required each time deforming and cutting is performed. The deforming procedure is not an infinite loop in a conventional sense. Rather, the procedure may be interrupted at any time to terminate the program.

Step 1: Preprocessing Procedure:

(1) Model Reading.

A system for implementing a disclosed embodiment method uses three types of models, including a standard triangular patch OBJ file, a standard texture image TGA file and a custom metaball SPH file. As external files, these are feed into the system which is designed with a special purpose data structure for storing data. The models are required for an organ, a scalpel and a surgical clamp. An advantage in using the models lies in that an initial state of the system may be initialized. The SPH file used herein is a file with a custom extension according to the present disclosure. The file keeps, in rows, a centroid position and a radius for each metaball. The file is generated by an external Voronoi diagram analysis program analyzing an OBJ file. The OBJ file is, in turn, a file typically used in storing a triangular patch. Each row is an information line indexed with a different letter, including vertex information and patch information. The vertex information may be further categorized into three types: vertex position information, vertex normal direction information and vertex texture coordinate information. The TGA file gives a specific color for a texture pixel.

(2) Initialization of Rendering

This phase requires setting up OpenGL rendering configuration. Various models that need rendering are placed into a rendering pipeline list. At the same time, device environment of Phantom Device is enabled, and a device feedback force output is added.

(3) Initialization of Driving Method

The driving method mainly includes a position-based dynamics method and a meshless method, where the position-based dynamics method is initialized depending on positions and sizes of the input metaballs. An initialized object mainly has topology information depending on a stretch restraint. In the present disclosure, a metaball is allowed to intersect with others. Two intersecting metaballs are spatially continuous, and can be seen as if a topological connection is between them. Adding a unit restraint may allow the system to converge more quickly, where the unit restraint is obtained by analyzing the position and radius of each metaball. Each type of restraint requires initialization of a corresponding parameter.

Initializing the meshless method includes initializing a material parameter and a physical deforming parameter. The material parameter mainly initializes a Young's modulus Y and a Poisson's ratio nu. This parameter is a parameter in Hooke's law and determines a magnitude of change relating to strain and stress.

Step 2: Deforming Procedure:

(1) Volume Model Driving

Organ deformation refers to a change in shape when an organ is subject to an external force. The model will also be gradually restored and converged to a certain state when the external force is removed. In order to achieve the convergence, some of the metaballs are fixed in position to prevent movement, so that the model will converge towards the fixed metaballs when the model deforms.

Driving of the metaball model uses the position-based dynamics method. Compared with a conventional physical method, this method omits an acceleration calculation procedure. Speed and position of a vertex are immediately updated after the external force is applied. A predicted position is corrected through a series of restraints, and finally a movement position is determined. Restraints used in the present disclosure include a unit restraint, a stretch restraint and an energy restraint. The stretch restraint may produce a rapid convergence, the unit restraint may ensure a restoration of the original state upon a complete convergence, and the energy restraint and the meshless system create a coupling.

(2) Surface Binding

The surface binding refers to binding of the point set to the metaball. Since the coupling phase is relatively short, the surface binding in the present disclosure only targets at binding to the metaball. For each surface vertex, it is desired to bind the movement of the vertex to its surrounding metaballs. The binding may be smoothed using Gaussian binding. Specific steps of Gaussian binding are as the following. For each vertex, select a metaball meeting a criteria from all the metaballs, where the criteria is verified by: obtaining a distance d from the vertex to the centroid, obtaining the radius r of the metaball, calculating a ratio k=d/r, and selecting the metaball when k falls within a suitable range. As used herein, the range may be 1<=k<=2. Among all metaballs meeting the criteria, select three metaballs having the smallest k-s, the k-s being different from each other.

Step 3: Cutting Procedure

Figure 2:
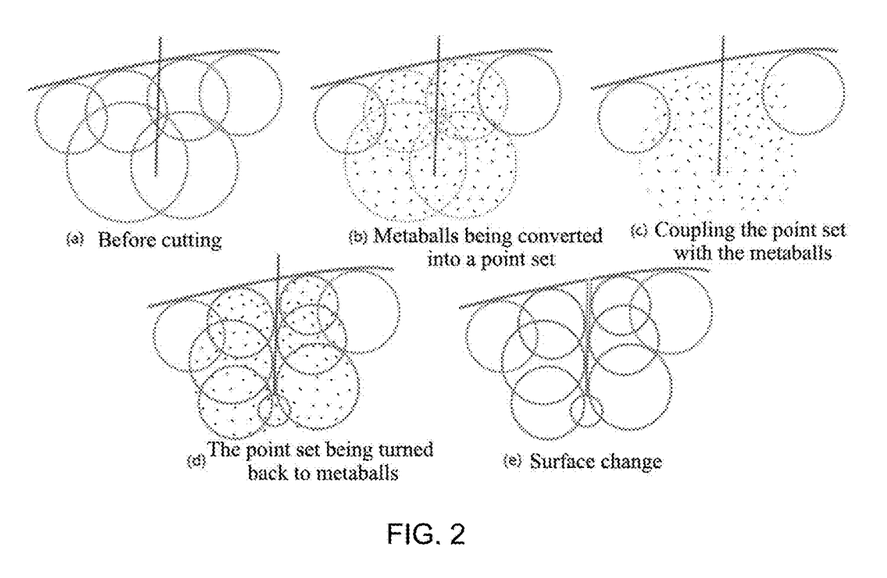
FIG. 2 is a schematic diagram illustrating a cutting mode, including a. before cutting; b. metaballs being converted into a point set; c. coupling the point set with the metaballs; d. the point set being turned back to metaballs; and e. surface change.

The cutting procedure is the center of the inventive concept of the present disclosure. FIG. 2 is a schematic diagram of the entire cutting procedure, where (a) in the drawing shows that a scalpel collides with the model, that is, the cutting starts, (b) indicates that the collided metaballs are converted into a point set and are removed, (c) indicates that the metaballs and the point set are coupling, (d) indicates that the point set is turned back to metaballs, and (e) represents a surface cutting condition.

(1) Metaball to Point Set

Once a metaball collide with the scalpel, the metaball needs to be converted into a point set. The present disclosure provides two methods for the point set conversion. One is uniform sampling, which uses a fraction of the smallest metaball radius among all the metaballs as a filling spacing, and obtains evenly spaced points along three coordinate axes. Typically, the uniform sampling is applicable to a case where the largest and the smallest radius of the metaballs do not differ much. When difference is great, larger metaballs will be filled with more points, which may hinder real-time feedback. In order to ensure smoothness when cutting in such situation, it is required to take samples with wide spacing in bigger metaballs, and with narrow spacing in smaller metaballs. The spacing may be assigned with a value according to a radius bracket into which the metaball falls.

Alternatively, the spacing may be assigned with a value according to the radius of the metaball, that is, each metaball is filled with a fixed number of points. When the second filling method is used, intersecting regions between metaballs will need special treatment in order to ensure that the points in the meshless system are spaced by no less than a given minimum value.

During actual cutting, a plane formed by the sweeping of a cutter is usually a relatively smooth curved surface which can be associated with a plurality of random factors and can be difficult to parameterize. Thus, the curved surface is discretized into a series of folding planes, that is, a series of planes with connected borders. Hence, collision detection in the system of the present disclosure is a collision between the folding plane and the metaball, and/or between the folding planes and the triangular patch.

In order to facilitate generation of the point set from the metaball cutting, space within the bounding box for the model is initially divided to obtain several mesh points that are equally spaced along all of the three axes. These mesh points are the sampling mesh points. When a metaball collides with a surgical plane, the mesh points inside the metaball are extracted, forming the point set for the metaball.

A metaball needs to be removed from its original region after being cut and converted into meshless particles. Since a topological relationship is established at the time of initialization due to a restraint on the metaball, subscripts of neighbors to the metaball are preserved. Thus, these subscripts need to be changed when physically removing the metaball. In case the metaball is logically removed, information about restraint from the metaball to other metaballs or vice versa is also removed, so as to ensure that the metaball will no longer affect other metaballs, nor could other metaballs affect the metaball, during subsequent integration.

(2) Driving of Point Set

A simplified meshless model is used for driving the point set. Instead of calculating energy at any and all positions, this model calculates energy at each mesh point, and considers the same energy applies to any and all positions within the space influenced by the mesh point. Compared with the conventional meshless method, this method simplifies the energy integration model. With a slight decline in accuracy, this model is greatly improved in speed for solving the integration.

This method uses a kernel function as below, $$\omega_h(r) = \frac{315}{64 \pi h^9} \begin{cases} (h^2 - r^2)^3, & 0 \le r \le h \\ 0, & r > h \end{cases}, \quad (1)$$

This kernel function is a cubic B-spline function, which describes that an influence range of a meshless point has a spherical distribution, and in this range, the closer to a center of metaball, the greater the influence. In this function, r represents a distance from the influenced point to the meshless point, which is a non-negative value. $\omega_h(r)$ indicates that the kernel function is evaluated in relation to r. h represents a support radius for each particle. h is a constant for a given meshless point, and indicates a maximum influence distance of the particle. Neighbor points for each point may be initialized according to the position distribution of the point set, and a support radius of each point is determined by the neighbor points. Typically, two times of the average distance of all neighbor points is selected as the support radius.

$\omega_h(r)$ is calculated by using initial state of meshless points. Thus, for each pair of points, $\omega_h(r)$ is a fixed value, and thus may be represented as $\omega_{ij}$, where the subscript i represents the meshless point being calculated, and the subscript j represents a neighbor point of this point.

In order to calculate a position in a next frame, the calculation begins from a deformation gradient, then a strain according to the gradient, and then a stress according to Hooke's law. With the stress and the strain, energy density can be obtained. By multiplying the energy density by a volume coefficient, energy can be obtained. By integrating the energy relative to the displacement, the force applied to a point can be obtained. The force may be transformed into displacement by either explicit integration or implicit integration. The gradient is calculated as below:

$$\nabla u(x_i) = A_i^{-1} \Sigma_j \omega_{h_j}(\|x_{ij}\|) j, \quad (2)$$

where u represents the displacement, $\nabla u$ represents a gradient matrix of this displacement, $\nabla u(x_i)$ represents a gradient value at a point $x_i$, and the subscript i represents the meshless point being calculated. $\omega_h(r)$ is a kernel function, where the subscript indicates that each meshless point has its own kernel function. $x_{ij}$ represents a spatial vector from point $x_i$ to point $x_1$, where the subscript j represents a neighbor point of this point. Each meshless point has a plurality of neighbor points, thus a Sum function is used in the equation, indicating that weighted distance vectors $\omega_h(\|x_{ij}\|)x_{ij}$ of all neighbor points are added together. A is referred to as a base matrix, with a subscript indicating that each mesh point has its own base matrix. The base matrix is only related to an initial position and a neighbor position of each point, $$A_i = \Sigma_j \omega_{h_j}(\|x_{ij}\|) x_{ij} x_{ij}^T, \quad (3)$$

After obtaining the gradient, the strain and the stress may be calculated, $$\varepsilon = J^T J - I = \nabla u + \nabla u^T + \nabla u \nabla u^T, \sigma = C\varepsilon, \quad (4)$$

where $\varepsilon$ is the strain, and $\sigma$ is the stress. J is a Jacobian matrix, which is a result of the gradient matrix $\nabla u$ plus a unit matrix I. A gradient representation of the strain may be derived by substituting $J = \nabla u + I$ into the equation $J^T J - I$. After obtaining the strain, the stress may be calculated. In Hooke's law, the stress and the strain have a linear relation. C is a fourth-order tensor matrix, which is related to material parameters such as Young's modulus and Poisson's ratio.

After the strain and the stress are obtained, the energy density at the position may be obtained, $$U = \frac{1}{2}(\varepsilon \cdot \sigma) = \frac{1}{2}\left(\sum_{i=1}^{3}\sum_{j=1}^{3}\varepsilon_{ij}\sigma_{ij}\right), \quad (5)$$

where U represents the energy density at the meshless point. Since the energy density at that point is only dependent on the strain and stress at the point, this equation does not include subscript. The strain matrix $\varepsilon$ and the stress matrix $\sigma$ are 3*3 matrices. The $\varepsilon_{ij}$ and $\sigma_{ij}$ on the right hand side of the Equation (5) represent values of the strain matrix and the stress matrix in row i and column j, respectively. The energy density means energy per unit volume, through which a force per unit volume may be obtained by simply calculating a derivation relative to the displacement, $$f = -\nabla_u U = -\frac{1}{2}\nabla_u(\varepsilon \cdot C\varepsilon) = -\sigma\nabla_u\varepsilon, \quad (6)$$

where $\nabla_u$ represents obtaining the gradient from the displacement u. By bring in the Equation (5), a simplified equation for the force per unit volume may be obtained, which is a negative stress matrix multiplies the gradient $-\sigma\nabla_u\varepsilon$ of the strain matrix relative to the displacement.

In order to obtain a further form of force equation, the Equation (4) is substituted into the Equation (6) to obtain a spatial vector representation of the force equation. Meanwhile, the force of a central mesh point i is distinguished from the force of its neighbor mesh point j. According to the reactive nature of force, the force applied to i is the reverse of the total force on j, $$F_j = -\nabla_{u_j} U_i = -V_i \sigma_i \nabla_{u_j} \varepsilon_i = -2V_i J_i \sigma_i d_j = F_e d_j,$$

$$F_i = \Sigma_j f_j = -2V_i J_i \sigma_i d_i = F_e d_i, \quad (7)$$

where V represents volume, J is a Jacobian matrix, and $\sigma$ is the stress. It can be seen that $F_j$ and $F_i$ share several common items which may be represented by $F_e = -2V_i J_i \sigma_i$. This item is only affected by particle i, where $d_i$ and $d_j$ are, respectively, items representing influence ranges, $$d_j = A^{-1}(x_{ij}\omega_{ij}),$$

$$d_i = A^{-1}(\Sigma_j x_{ij}\omega_{ij}), \quad (8)$$

where A is a base matrix, $x_{ij}$ represents a spatial vector from point $x_i$ to point $x_j$, and $\omega_{ij}$ is a simplified representation for the kernel function. In combination with the Equations (7) and (8), the stress may be calculated directly from a change in the spatial position. After calculating the stress, parameters such as acceleration, velocity and displacement may be obtained according to Newton's third law, and thus a position in the next frame may be calculated according to the current position. This is the explicit integration approach. During actual tests, it is discovered that an alternating explicit integration method may lead to a better outcome. The method starts from setting up a time step, obtains a force in half of the time step, obtains a displacement based on the force, and updates a speed in the last half of the time step. In this way, the overall speed is slightly large, and the displacement is slightly small, creating a relative trade-off.

By using the above driving method, positions of all mesh points may be updated once each time the deforming procedure is reached, and driving of the point set is achieved.

(3) Coupling of Hybrid Driving System

To construct a meshless system from a point set, the first step is to construct a neighbor relationship. To a point set for a meshless system, cutting of a point is actually a change in the neighbor relationship, i.e., the virtual topological relationship, of the point. Therefore, to construct the neighbor relationship for the meshless system used in the present disclosure, it is desired to select a point pair that is not on different sides of the cutting plane. That is, the present disclosure realizes virtual topological cutting of the meshless points during the construction of the neighbor relationship.

Figure 3:
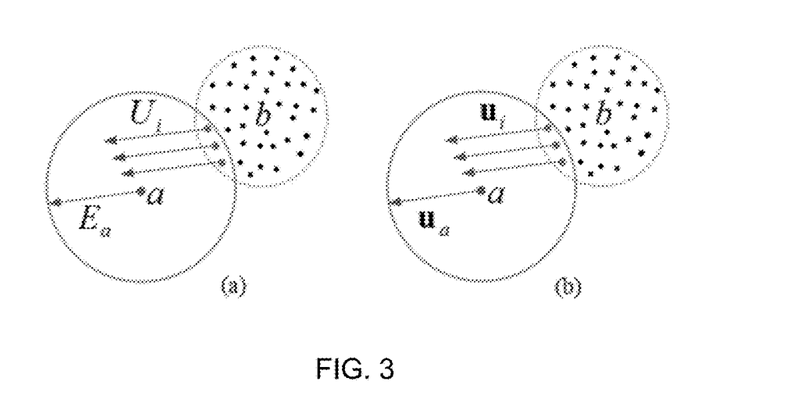
FIG. 3 illustrates the coupling of a point set with a metaball.

When both a metaball driven by the position-based dynamics and a point set driven by the meshless system are presented in the present disclosure, movement of one system needs to be transferred to the other system. As shown in FIG. 3, since the point set is generated from an initial metaball, part of the points are located within the remaining metaballs, and may be used as junction points for the coupling. When the metaball moves, points in the metaball need to make the same movement. Such movement is input from movements in the meshless system. Thus, a feedback from a metaball movement to a point set movement is created. When the point set moves, it is usually a small movement. By means of adding an energy constraint, the movement feedback from the point set to the metaball is achieved.

(4) Generation of Metaball Using Voronoi Diagram

In the meshless system used in the present disclosure, each point has a normal direction value which points from the centroid of the metaball, from which the point is created, to the actual position of the point. Boundary points may be determined by comparing angles between the normal direction and all neighbor vectors of the points.

Figure 4:
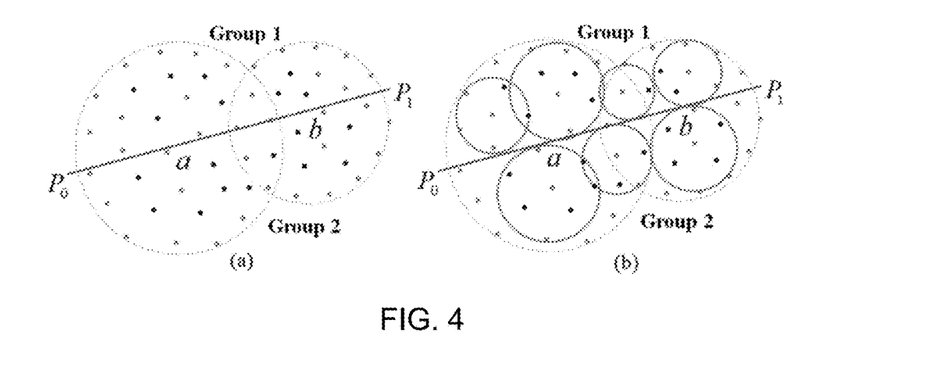
FIG. 4 is a schematic diagram illustrating metaball generation.

A Voronoi diagram analysis is applied to the boundary points to produce a set of partitioning facets that surround individual boundary points, and a vertex of each partitioning facet serves as a centroid for establishing a new metaball in the system. The radius for the new metaball is the shortest distance from the centroid to the boundary points or to an established metaball. The procedure may be illustrated in FIG. 4.

(5) Surface Splitting

Figure 5:
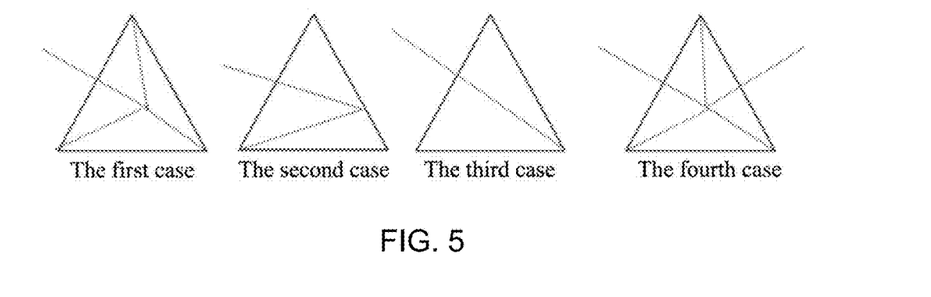
FIG. 5 is a schematic diagram illustrating intersection of a triangle and a folding plane.

Triangular mesh splitting targets at a split after an existing triangular mesh collides with the scalpel plane. There are different splitting results according to different situations of collisions between a triangle and a folding plane. The splitting is shown in FIG. 5.

The first case shows that the folding plane intersects with the triangle at an edge and an internal point. Of course, it is also possible to intersect at a vertex and an internal point, a situation which usually happens at the boundary of the folding plane, that is, a starting point of the cutting position. The second and third cases are more common, where the triangle only intersects with the folding plane at a self-plane. In these cases, the splitting may be done using a corresponding splitting method. The fourth case is trickier because a triangle is subject to a collision at an intersection of two planes. The number of triangles that need to be generated from the triangle is also increased by one as compared to the first case. In fact, various cases are possible when processing the triangles. Additional vertex is needed even when the triangle intersects at only one boundary because the boundary needs to move towards two directions after the splitting, hence two groups of vertexes are necessary.

Figure 6:
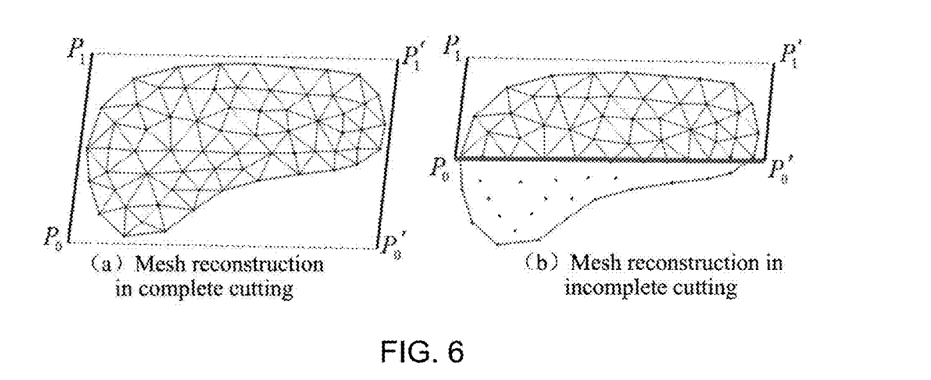
FIG. 6 is a schematic diagram illustrating interior node triangularization, including (a) full boundary; (b) semi-boundary.

To create a fissure is in fact to generate a cut folding plane, except that the plane needs to be restricted within the original triangular mesh. The present disclosure selects a meshless boundary point close to the folding plane, projects the boundary point onto the folding plane. Together with the boundary points generated after the triangle splitting in the previous step, these points are subject to boundary-limited triangularization. The boundary-limited triangularization is actually to remove any triangle outside the boundary after all points have been triangularized. FIG. 6 is a schematic diagram illustrating this method.

Since the vertexes used in the triangularization are generated during the splitting step, the triangles generated from the triangularization are connected to triangles generated from the splitting. After being generated, all mesh points need to be bound to a metaball, and the binding is again Gaussian binding, where an appropriate metaball is selected, and Gaussian weight is assigned according to its distance to the mesh point.

Step 4: Rendering Procedure (1) Surface Rendering

The surface rendering refers to rendering a surface triangular patch. OpenGL is used as a rendering library, and connections between vertexes are determined by reading triangle edge information from an OBJ file. The actual position of a vertex may be changed after a deforming or cutting. Accordingly, the drawing procedure is a dynamic one, where a rendering procedure takes place each time a deforming procedure or cutting procedure occurs.

A basic method to render the triangular patch with the OpenGL is to: firstly, specify that the drawing object is a triangle, and then specify vertex information for each triangle, and specify normal direction and texture coordinates before specifying a position.

In Phantom Device, tactile is created by drawing object information into the device in a way same as that in OpenGL. After the object information is drawn into the device, the device may perform a tactile feedback.

(2) Drawing of Volume Model

A volume model includes a metaball model and a metaball topology. To draw a metaball is to simply draw a ball. For the convenience of viewing, it is most desirable to setup a transparency level. The metaball topology is represented by a line segment joining centroids of two metaballs to indicate that there is a topological relationship between the two metaballs. This topology means that when one metaball moves, the other metaball will be driven to move, which is a representation of the stretch constraint.

It is usually very time consuming to draw a volume model because OpenGL will perform a great deal of segmentations when drawing the ball. Hence, the present disclosure typically selects to not display the volume model except for viewing cutting effects of the metaballs. In addition, there is no need to draw any volume model in the tactile device.

The following is a test result for verifying the performance of the disclosed method for real-time cutting of a digital organ based on a metaball model and a hybrid driving method.

Table 1 shows a comparison between time consumed on various models during the deforming and cutting procedures, as well as the number of metaballs filled therein. It can be seen that a model does not typically need too many metaballs, thus the deformation is very fast. The number of models filled is about one tenth of the tetrahedral or hexahedral model.

TABLE 1

Comparison among various models

| | Vertex # | Metaball # | Deforming Time per Frame (ms) | Cutting Time per Frame (ms) |
| --- | --- | --- | --- | --- |
| Liver | 8128 | 570 | 6.25 | 9.52 |
| Spleen | 1480 | 466 | 2.14 | 2.58 |
| Cholecyst | 1415 | 452 | 2.65 | 3.33 |
| Steak | 1266 | 539 | 1.8 | 2.4 |

Figure 7:
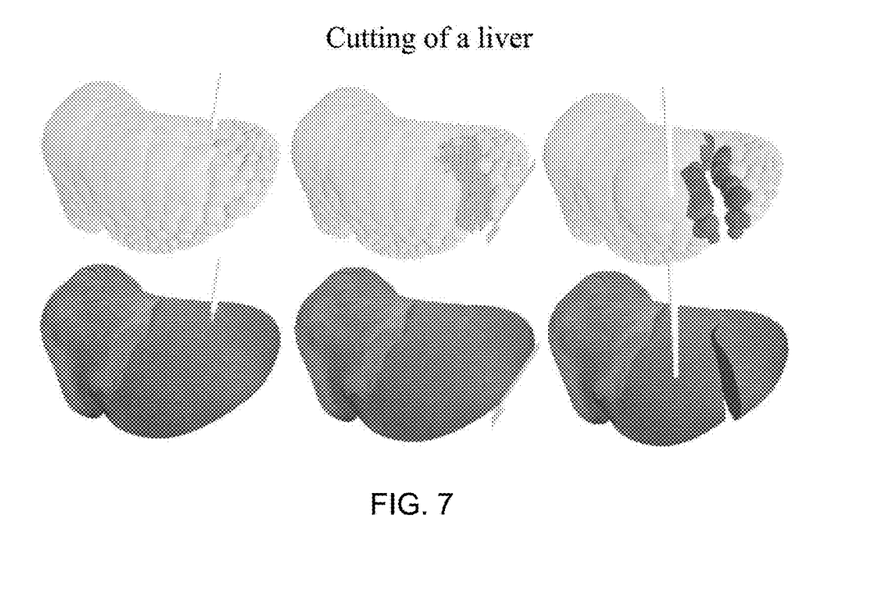
FIG. 7 illustrates a cutting result for a liver (the upper row showing volume models, while the lower row showing surface models)
Figure 8:
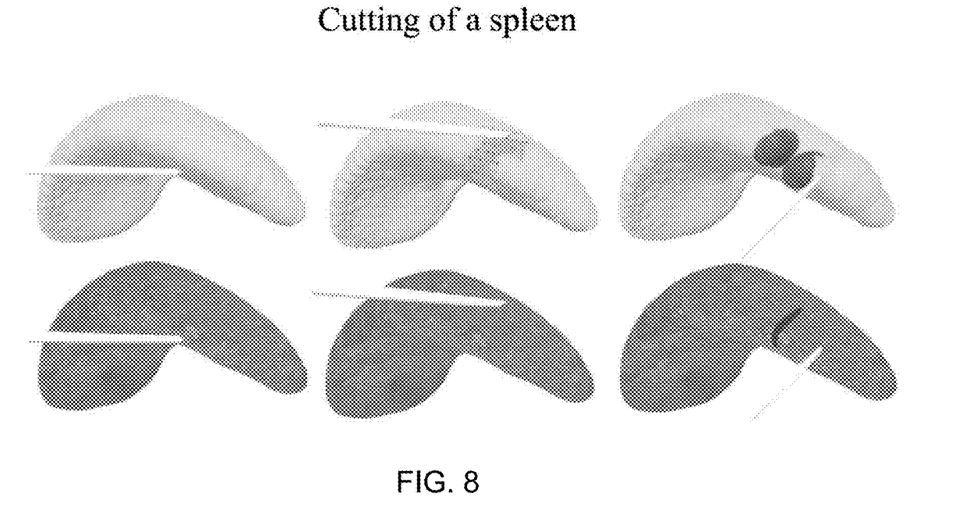
FIG. 8 illustrates a cutting result for a cholecyst (the upper row showing volume models, while the lower row showing surface models)
Figure 9:
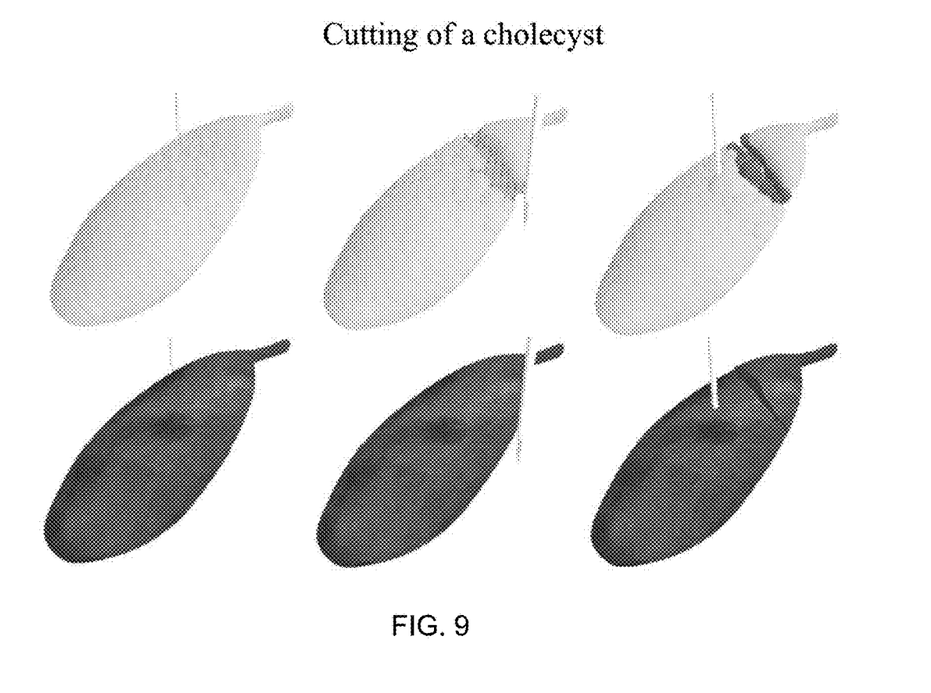
FIG. 9 illustrates a cutting result for a spleen (the upper row showing volume models, while the lower row showing surface models)
Figure 10:
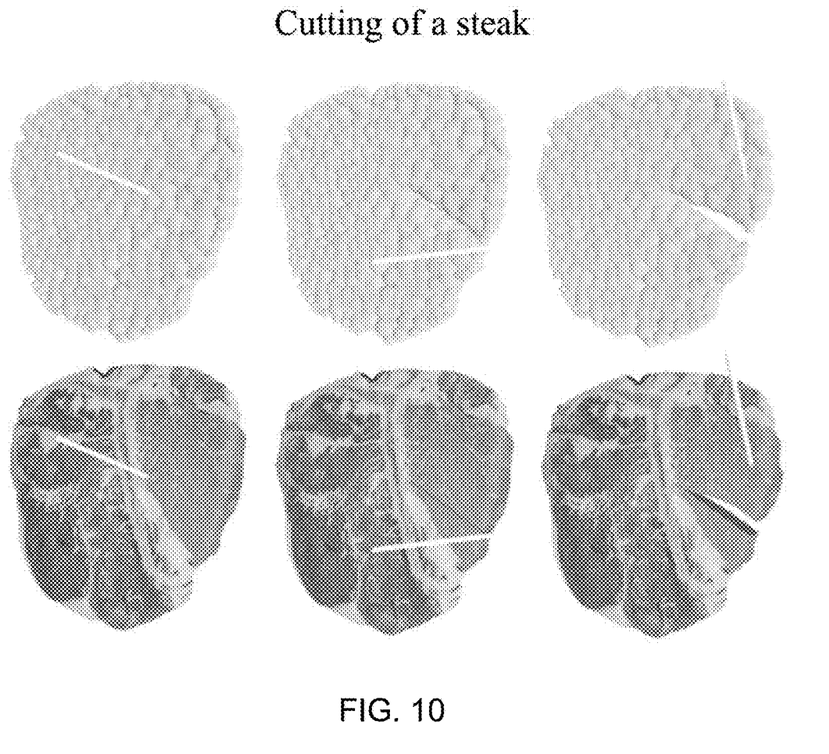
FIG. 10 illustrates a cutting result for a steak (the upper row showing volume models, while the lower row showing surface models).

FIGS. 7-10 demonstrate cutting effects for four types of models, where FIG. 7 shows cutting of a liver, FIG. 8 shows cutting of a spleen, FIG. 9 shows cutting of a cholecyst, and FIG. 10 shows cutting of a steak. In each of the four figures, the first row is from metaball cutting, and the second row is from surface cutting.

It can be clearly seen from the outcomes in the figures that no additional metaball is generated while splitting the metaball, and that the newly-generated metaballs have, on average, a size of about half of the metaballs before the splitting, and their number is about doubled, an outcome consistent with expectations of the present disclosure. In this case, the cutting will not become a bottleneck to the deforming, and will not hinder the iteration speed or convergence speed.

The present disclosure focuses on authenticity and smoothness of the post-cutting movement. As can be seen from the figures, there is no obvious jaggedness. The cutting edge is smooth, and shows no obvious dent, even when the cutting edge is curved.

The present disclosure also compares the cutting performance with conventional approaches. A first approach uses a finite element method to drive a finite element model (Yang C., Li S., Wang L., Hao A. and Qin, H., *Real-time physical deformation and cutting of heterogeneous objects* via *hybrid coupling of meshless approach and finite element method*, Computer Animation and Virtual Worlds, 25(3-4), 423435, (2014)). A second approach uses a position-based dynamics method to drive a tetrahedral model (Pan J., Bai J., Zhao X., Hao A. and Qin H., *Real-time haptic manipulation and cutting of hybrid soft tissue models by extended position-based dynamics*, Computer Animation and Virtual Worlds, 6, 321335, (2015)). The approaches are compared in cutting a steak.

TABLE 2

Comparison in steak cutting

| Approach | # of deformed elements | Deforming Time per Frame (ms) | Cutting Time per Frame (ms) |
| --- | --- | --- | --- |
| 1st approach | 6272 | 25.2 | 8.6 |
| 2nd approach | 1477 | 1.7 | 6.5 |
| This disclosure | 539 | 1.5 | 2.4 |

By comparing data in the table, it can be clearly seen that the present disclosure has obvious advantage in terms of deforming speed and cutting speed, and the advantage is even more pronounced in terms of real time responsiveness. When a video comparison is made with the approaches of the two articles, it can be clearly seen that the disclosed method also has an advantage in faster convergence speed. In addition, neither of the above approaches demonstrates any excessive increase in speed when splitting the model. Therefore, after the cutting is performed for a period of time, the advantages of the present disclosure will be more clearly demonstrated, and the deforming and convergence speeds will not be abruptly shortened.

Technical contents not elaborated herein belong to technologies known to persons of ordinary skill in the art.

Although specific embodiments of the present disclosure have been described illustratively hereinabove for facilitating understanding of the present disclosure by persons of ordinary skill in the art, it shall be appreciated that the present disclosure is not limited to the scope of the specific embodiments. It shall be apparent to persons of ordinary skills in the art that various changes may be made without departing from the spirit and scope of the present disclosure as defined and determined by the appended claims. Any and all creation based on the present inventive concept shall fall into the protection scope of the present disclosure.

What is claimed is:

1. A method for real-time cutting of a digital organ based on a metaball model and a hybrid driving method used in virtual surgery, comprising:

Step 1: a preprocessing procedure, comprising: reading a model to be processed, wherein the model comprises a metaball model and a surface model, the metaball model being a physical model configured for driving, and the surface model being a geometrical model configured for rendering; the preprocessing procedure further comprises initializing a rendering environment and a deforming method;

Step 2: a deforming procedure, comprising: performing a position-based dynamics method driving according to data obtained by reading the model as in the Step 1, wherein the deforming procedure is a loop procedure in that the deforming procedure repeats at the end of the processing unless a cutting procedure in Step 3 is performed or a scalpel is disengaged from the surface of the model;

Step 3: a cutting procedure, contingent upon a cutting event which occurs at the end of Step 2 when a scalpel collides with the metaball model, comprising: going to the deforming procedure of Step 2 if the scalpel is not disengaged from the surface of the model at the end of the cutting procedure, wherein the cutting procedure comprises a cutting mode that converts a metaball to a point set and then back to a metaball using a hybrid deforming and driving processing procedure, wherein a metaball cutting comprises four parts, which are, firstly, converting collided metaball into a point set; then constructing a meshless system using the point set while coupling the remains of the metaball system and the meshless system; and finally, converting the point set into a metaball; and a surface cutting, which occurs together with the metaball cutting, comprises splitting a surface, generating a fissure and re-binding; and Step 4: a rendering procedure, which has been ready starting from the Step 1, requires data input from the deforming procedure or the cutting procedure as the Step 2 and the Step 3 proceed, performs rendering constantly, and finally outputs a display image corresponding to the model;

wherein the Step 1 preprocessing procedure comprises:

(1) reading three types of pre-established files comprising a standard triangular patch OBJ file, a standard texture image TGA file and a custom metaball SPH file, wherein the SPH file is generated via the OBJ file, the SPH file provides metaball information which comprises metaball centroid position and radius information; the OBJ file stores vertex information and patch information of a triangular patch in a generic form; the TGA file stores texture information; and data read from the three types of files are stored using a corresponding data structure, respectively;

(2) initializing the rendering environment, comprising constructing an OpenGL rendering environment and initializing a rendering environment for a 3D tactile device Phantom Device; and (3) initializing a physical driving method, comprising initializing a parameter for the position-based dynamics method and a meshless method;

wherein the Step 3 cutting procedure comprises:

(1) converting the metaball into the point set when a scalpel collides with the metaball, while removing any collided metaball to generate a residual metaball system;

(2) constructing the meshless system using the point set generated in Step (1); performing the driving using a meshless method which is a simplified meshless method;

(3) performing the hybrid driving using the residual metaball system generated in Step (1) and the meshless system generated in Step (2), wherein the two systems are coupled in that movement in one system causes movement information being fed back to the other system;

(4) restoring the point set back to a metaball when the scalpel disengages from the metaball model, wherein the restoring is realized by collecting a meshless point on a cut surface, analyzing the vertex using a Voronoi diagram to obtain a central skeleton, and filling the skeleton with a metaball;

(5) splitting a surface into a triangle based on various conditions in which a scalpel cutting line intersects with the triangle, wherein the splitting follows a basic principle, that is, a split surface remains being filled with a triangle, polygons on different sides of the cutting line are separately split into triangles; collecting a meshless point at a fissure; triangulating the meshless point to generate a fissured mesh; and updating binding condition for all triangles, including newly generated triangles and triangles near the fissure; and (6) executing the above steps according to the following time logic: performing Step (1) when the scalpel collides with the metaball, and potentially repeating the step for several times; proceeding to Step (2) and Step (3) immediately after each time Step (1) is performed, wherein the cutting is completed when no more collision occurs between the scalpel and the metaball; proceeding to Step (4); performing the Step (5) in parallel with other steps because the splitting is required whenever the scalpel collides with the surface; generating the fissure while restoring the metaball in Step (4); and performing re-binding after both Step (4) and the fissure generation are completed.

2. The method for real-time cutting of a digital organ based on a metaball model and a hybrid driving method according to claim 1, wherein the Step 2 deforming procedure comprises:

(1) driving the metaball using the position-based dynamics (PBD) method according to the data obtained by reading the model as in the Step 1; adding a stretch restraint, a unit restraint and an energy restraint into the position-based dynamics method; and arranging fixed metaball in order to achieve convergence; and (2) establishing Gaussian binding between a vertex of a surface triangular patch and a metaball, so that the movement of the vertex is determined by the movement of at most 3 metaballs surrounding the vertex, wherein the determination is such that a Gaussian value for a ratio of a distance between a metaball centroid and the vertexes to the radius is applied with a weight upon the vertex.

3. The method for real-time cutting of a digital organ based on a metaball model and a hybrid driving method according to claim 1, wherein the Step 4 rendering procedure comprises:

(1) drawing surface information for the model, wherein the surface information comprises three parts: texture information, vertex information and patch information, initial information of the surface has been given when the mode is read, the texture information remains unchanged, the vertex information is changed continuously during the deforming procedure and the cutting procedure, the patch information is also changed during the steps of the cutting procedure, the rendering procedure accompanies both the deforming procedure and the cutting procedure, the surface information needs to be drawn twice, one on a screen using OpenGL, another drawn into a force feedback device using a Phantom library;

(2) selectively drawing volume information; providing a volume drawing switch; opening the volume information for drawing when viewing a cutting effect, wherein the volume information comprises the metaball information and metaball topology information, the metaball information being given during the preprocessing procedure when the model is read, and later being continuously changed during the steps of the deforming procedure and the cutting procedure, the metaball topology information indicating the intersection between the metaball in that a line segment connects the centroids of intersecting metaballs to indicate the existence of topology information therebetween.

* * * * *